US008126556B2

United States Patent
Hjelm et al.

(10) Patent No.: US 8,126,556 B2
(45) Date of Patent: Feb. 28, 2012

(54) MEDICAL IMPLANTABLE DEVICE AND METHOD FOR CONNECTING AN ANTENNA TO THE SAME

(75) Inventors: Stefan Hjelm, Bålsta (SE); Tomas Snitting, Stockholm (SE); Wisit Lim, Palmdale, CA (US); Kavous Sahabi, Winnetka, CA (US)

(73) Assignee: St. Jude Medical AB, Jarfalla (SE)

( * ) Notice: Subject to any disclaimer, the term of this patent is extended or adjusted under 35 U.S.C. 154(b) by 834 days.

(21) Appl. No.: 12/091,631

(22) PCT Filed: Oct. 27, 2005

(86) PCT No.: PCT/SE2005/001625
§ 371 (c)(1),
(2), (4) Date: Sep. 16, 2008

(87) PCT Pub. No.: WO2007/050002
PCT Pub. Date: May 3, 2007

(65) Prior Publication Data
US 2009/0163979 A1    Jun. 25, 2009

(51) Int. Cl.
*A61N 1/08* (2006.01)
(52) U.S. Cl. ............................................ 607/36; 607/37
(58) Field of Classification Search .................... 607/36, 607/37, 60; 439/909
See application file for complete search history.

(56) References Cited

U.S. PATENT DOCUMENTS

| 2004/0215280 A1* | 10/2004 | Dublin et al. ................ 607/36 |
| 2005/0113886 A1 | 5/2005 | Fischell et al. |
| 2005/0134520 A1 | 6/2005 | Rawat et al. |
| 2005/0203584 A1 | 9/2005 | Twetan et al. |

FOREIGN PATENT DOCUMENTS

| EP | 1 582 235 | 10/2005 |
| EP | 1 695 736 | 8/2006 |

* cited by examiner

*Primary Examiner* — Carl H. Layno
*Assistant Examiner* — Tammie K Heller
(74) *Attorney, Agent, or Firm* — Schiff Hardin LLP

(57) ABSTRACT

In a medical implantable device having a hermetically sealed, radio shielded encapsulations containing an RF circuit therein and having an antenna located outside of the encapsulation, and in a method for connecting the RF circuit to the antenna, at least one hermetical feedthrough connection is provided in the form of at least one conductor passing through a wall portion of the encapsulation in a liquid-tight and gas-tight manner, with the feedthrough being electrically insulated from the encapsulation. At least one connector pin is provided on an RF circuit board, which is resiliently mounted on the RF circuit board. The RF circuit is mounted in the encapsulation so as to cause the connector pin to resiliently engage the conductor and to electrically connect the conductor with the RF circuit board.

7 Claims, 2 Drawing Sheets

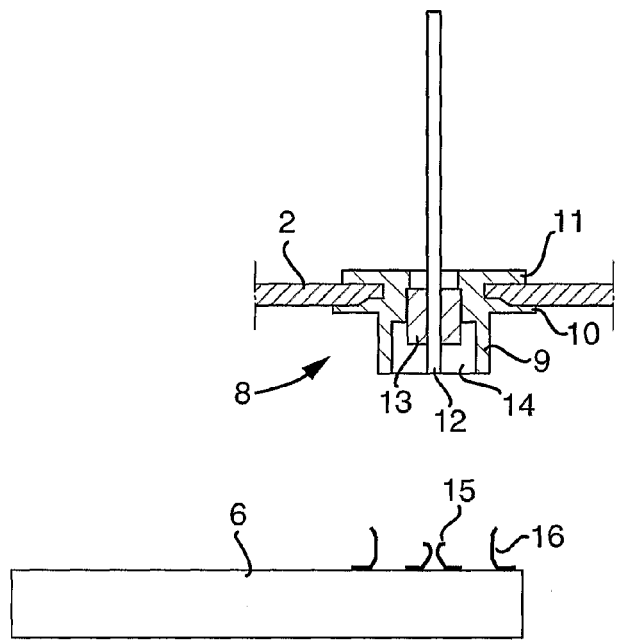
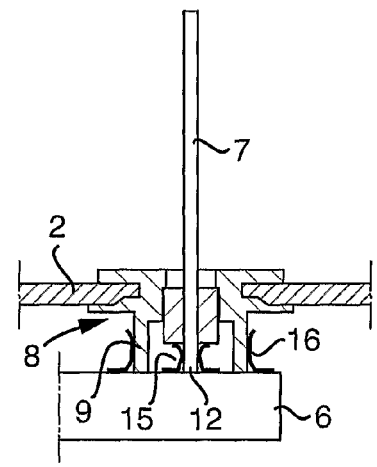
Fig 2
Fig 3
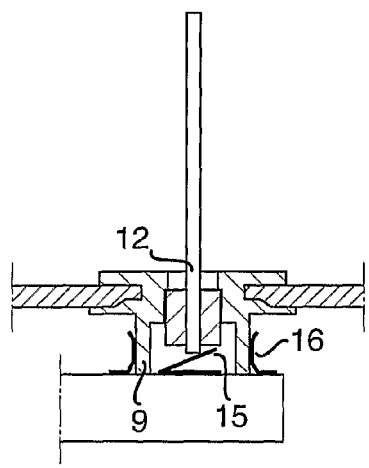
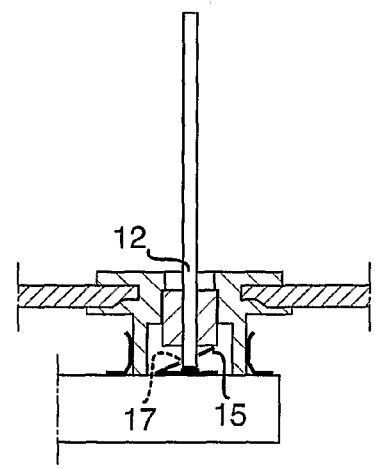
Fig 4
Fig 5

MEDICAL IMPLANTABLE DEVICE AND METHOD FOR CONNECTING AN ANTENNA TO THE SAME

BACKGROUND OF THE INVENTION

1. Field of the Invention

The present invention relates to a medical implantable device of the type having a hermetically sealed, radio shielded encapsulation, which is adapted to be implanted inside living tissue, and an RF-circuit positioned inside the encapsulation for communication with an RF-device outside the tissue, the RF-circuit being connectible to an antenna located outside of the encapsulation, via at least one hermetical feed through in the form of at least one conductor passed through a wall portion of the encapsulation in a liquid and gas tight manner and electrically insulated from the encapsulation.

The invention also relates to a method for connecting an RF-circuit inside a hermetically sealed, radio shielded encapsulation, to an antenna located outside the encapsulation.

2. Description of the Prior Art

It is becoming more and more common to communicate wirelessly with medical implantable devices, such as pacemakers, implantable cardioverter defibrillators (ICD's) or insulin pumps, which contain electronic circuits and are implanted inside tissue of human or animal bodies. In this way it is possible to monitor the function of the medical implantable device itself and/or an organ inside the body, e.g. the heart, to reprogram the device without removing it from the body in case the conditions should change, or to perform medical or therapeutic treatment on demand by means of the device inside the body, such as electrical shocks, so called defibrillation, to restart a heart that has stopped, or to request injection of a dose of insulin.

Up to now the most common way to accomplish this communication has been to use inductive telemetry. However, inductive telemetry has its limitations with regard to range and transmission speed. Therefore radio frequency transmission is considered to be a better alternative, i.e. to provide the medical implantable device with a radio transmitter and/or receiver (transceiver), hereinafter called a radio frequency circuit or RF-circuit, for enabling communication with a corresponding transmitter and/or receiver (transceiver), hereinafter called radio frequency device or an RF-device, outside the tissue.

However, when performing radio frequency communication the connection and shielding issues become more critical and an antenna connected to the RF-circuit is required. In order to avoid interference in the electronic circuits inside the medical device from external radiation sources, it is common practice to make the encapsulation of the medical implantable device not only gas and fluid tight, but also radio shielded. This is most easily accomplished by manufacturing the encapsulation of a metal, such as a titanium steel alloy, but it may also be accomplished by providing an electrically insulated material, such as a ceramic or a resin, with a shielding material, which can be applied as an inner or outer foil or coating or as an embedded netting. Thus, the antenna has to be positioned outside the radio shielded encapsulation, to be able to communicate with the RF-device, and a gas and liquid tight as well as electrical insulated feed through has to be formed through the wall of the encapsulation for the antenna connection. For manufacturing reasons, the encapsulation with the feed through and the RF-circuit board are manufactured separated from each other and then assembled together at a later stage.

It is always desirable to make the implantable devices as small as possible to minimize discomfort for the persons who have to carry them. This applies also to the RF-circuit board which normally has the size of only about 30-100 $mm^2$, and it has to be positioned very close to other components inside the encapsulation. Thus, the space for accomplishing the connection between the RF-circuit board and the feed through to the antenna will be very limited. At the same time, when using radio frequencies in the UHF region, which is preferred, it is crucial that the connection will be of a good quality having low inductance and stray capacitance. Moreover, it is important that the connection from the encapsulation wall to the RF-circuit board will be shielded over as long a part of its length as possible to prevent radiation from the RF-circuit from interfering with other electronic circuits within the encapsulation. It is also advantageous to keep the distance between the actual antenna outside the encapsulation and the RF-circuit board as short as possible, i.e. to position the RF-circuit board as close as possible to the feed through and the encapsulation wall.

The above criteria create problems during assembling since traditional methods for providing reliable electric connections all have certain drawbacks. For example, soldering, resistance welding, laser welding and the like, creates heat which could damage the electronic circuits, especially since they are packed so tightly together. The lack of space also makes it difficult for equipment adapted for this kind of connecting methods, to get access to the connection. Such connections also make replacement of the RF-circuit board complicated or impossible if that should for any reason be desired. Moreover, those connection methods are quite expensive to perform since they require a separate manufacturing step as well as expensive equipment.

SUMMARY OF THE INVENTION

An object of the present invention is to alleviate the aforementioned problems and disadvantages associated with prior art implantable medical devices. More particularly, the invention aims at providing a medical implantable device having an RF-circuit which is connectible to an antenna in a reliable, space saving and releasable way.

The invention also relates to a method for connecting an RF-circuit to an antenna, having basically the same object as above.

The above object is achieved in accordance with the invention by a medical implantable device having at least one conductor, which is passed through a wall portion of an encapsulation of the device in a hermetical way, an RF-circuit board that has at least one connector pin which is resilient or resiliently mounted on the RF-circuit board, such that the connector pin resiliently engages the conductor in the mounted state of the RF-circuit board in the encapsulation.

The invention may be implemented in many different ways. The feed through, which is passed through the wall portion of the encapsulation, has at least one conductor and one shielding surrounding the conductor. This is the case when using a so called monopole antenna. The shielding and isolation of the conductor when passing through the encapsulation wall, is very important in this case since a conducting layer, a so called ground plane, in the encapsulation, is utilized as a part of the antenna. However, it is important also of course for achieving a correct tuning of the antenna to the desired frequency as well as to prevent undesired disturbing radiation from outside to enter the RF-circuit or radiation from the RF-circuit to interfere with other electronic circuits inside the encapsulation.

The shielding around the conductor is often formed as a metallic sleeve, which is passed through the encapsulation wall and filled with an insulating and sealing ceramic material surrounding the conductor, which is concentrically located in the sleeve. To achieve sufficient shielding properties, it is important that the sleeve protrudes a distance inward from the inner surface of the encapsulation wall and preferably surrounds the connector substantially the entire distance to the surface of the RF-circuit board. This leaves very little or no access room for performing the connection of the connector with the RF-circuit board by means of soldering or welding. It would in theory be possible to leave a small open slot in the shielding sleeve in at least one direction without losing the essential shielding properties. However, as it is advantageous to form the component parts, including the sleeve, as small as possible, the available space would in practice be very limited.

According to the invention, the connection between the feed through conductor and the RF-circuit is accomplished by means of at least one connector pin, which is resilient or resiliently mounted on the RF-circuit board such that it will abut against or engage with the conductor in the mounted state of the RF-circuit board in the encapsulation. The connector pin may have any arbitrary, suitable form and can for instance have a flat or a curved cross section. As it is advantageous to form the conductor of a thin, and hence weak wire, it is preferred that the connector pin, when engaging the conductor in a radial direction, is adapted to interact with some kind of anvil member, which supports the conductor from the opposite direction in relation to the connector pin and prevents flexure of the conductor. This anvil member may preferably be one or more additional resilient or resiliently mounted connector pins. However, the anvil member could also be an arbitrary rigid member, either conductive or nonconducting, mounted onto the RF-circuit board.

In a preferred embodiment, two resilient connector pins are used, which are rigidly mounted in the RF-circuit board in such a way that they are suspended towards each other and located as well as formed such that the conductor will be introduced between the connector pins when mounting the RF-circuit board in the encapsulation. The longitudinal extension of the connector pins could be lateral to the extension of the conductor, but preferably it is parallel to the conductor. With a parallel longitudinal extension of the connector pins in relation to the conductor, it is possible and advantageous to perform the connection by means of three or more connector pins, which are distributed in a circle and resiliently suspended towards each other in order to achieve a centering action between the connector pins and the conductor.

As mentioned, the one or more connector pins may also be essentially rigid but resiliently mounted in the RF-circuit board, e.g. spring-loaded in the desired direction.

The connector pins discussed above, are all of a type which each abuts against an outer surface of the conductor and presses laterally against it in one direction, i.e. essentially a radial direction in relation to the conductor. The pressing force from the connector pin could, however, also be essentially in the longitudinal or axial direction of the conductor. One disadvantage with such an arrangement could be that the area of the conductor in the axial direction, i.e. the area of the end surface is very small which could lead to an insufficient electrical connection. Another that the resilient press force from the connector pin will tend to displace the RF-circuit board away from the conductor. However, this tendency could be prevented by some kind of means for displacement prevention of the RF-circuit board.

According to an alternative embodiment of the invention, the connector pin can have a longitudinal extension that is somewhat inclined in relation to the conductor, and having a through hole for the conductor with a diameter slightly larger than the conductor but somewhat misaligned or displaced in relation to the conductor. When moving the RF-circuit board toward the conductor, the conductor will be prevented from being introduced into the through hole in the connector pin due to the misalignment. The connector pin will therefore be resiliently deformed by the conductor until the conductor and the through hole will be aligned and the conductor may be passed through the hole. One additional advantage of such an arrangement is that when the conductor is positioned in the through hole, the RF-circuit will be hold by the connector pin and prevented from being displaced away from the conductor.

Two or more of the connector pin designs as discussed above, may be combined in one single device to achieve the desired properties.

The shielding sleeve may be electrically connected to the RF-circuit board in an arbitrary way. As the sleeve is better accessible from outside than the conductor, it would be possible to perform the connection in a conventional way by soldering or welding. However, in a preferred embodiment of the invention, the connection of the shielding is performed in a similar way as the connection of the conductor, i.e. by means of resilient or resiliently mounted connector pins, which abut and press against the surface of the shielding. In this way it is no risk of destroying any electrical components due to applied heat, and the connection will be easily disengageable if that for some reason would be desired, e.g. for replacement of defective components or circuits.

When connecting a dipole antenna or balanced antenna, having two separate antenna conductors, both antenna conductors may preferably be positioned in the same feed through in the encapsulation wall. Probably it would in such case, be advisable to provide a lead through sleeve having a wider diameter to ensure enough space for separate connection of each conductor.

BRIEF DESCRIPTION OF THE DRAWINGS

FIG. 2 is a schematic cross-section of a feedthrough in an enclosure and a portion of an RF circuit board, in an unassembled state.

FIG. 3 is a cross-section of the components shown in FIG. 2, in an assembled state.

FIG. 4 is a cross-section of a further embodiment of the connection between the feedthrough and the RF circuit board in accordance with the present invention.

FIG. 5 is a cross-section of another embodiment of the aforementioned connection.

DESCRIPTION OF THE PREFERRED EMBODIMENTS

Figure 1:
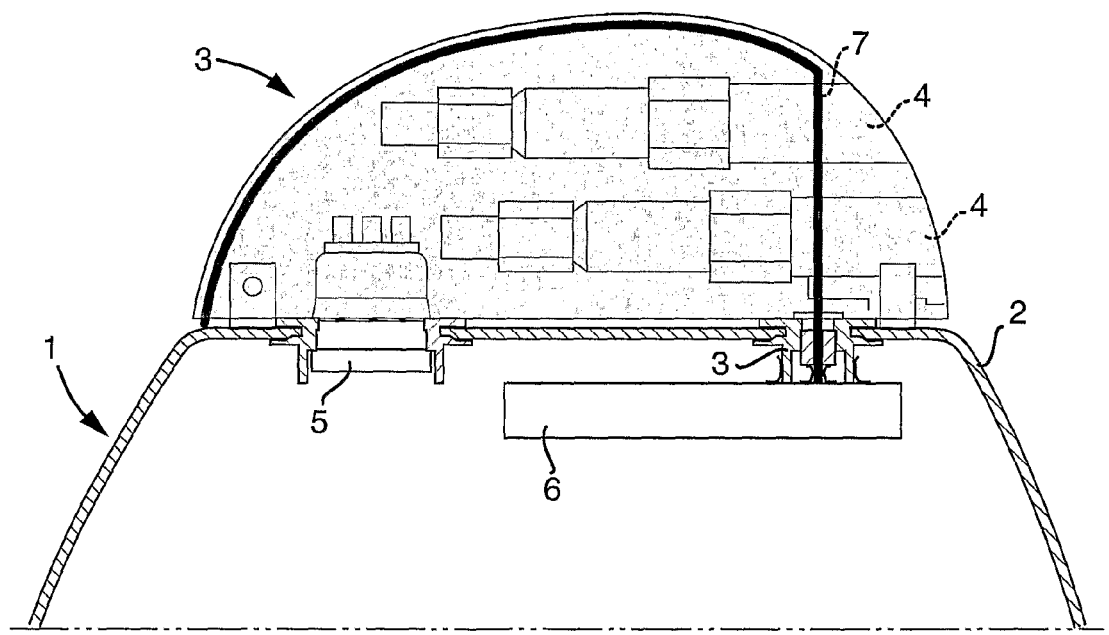
FIG. 1 is a schematic sectional view of a portion of a pacemaker embodying an antenna in accordance with the present invention.

FIG. 1 shows, in a schematic, cut through plan view, an example of a medical implantable device in form of a pacemaker. The pacemaker comprises a hermetically sealed, gas and water tight encapsulation 1, in which all electric and electronic circuits, such as control equipment, battery and the like, are positioned. Only a part of the encapsulation is shown in the drawing. The encapsulation has an outer shell in form of a wall 2 of a strong and durable material, preferably a metal such as a titanium steel alloy. During assembly of the pacemaker, the shell is divided into two separate shell parts into which the electronic components are mounted. Then the shell parts are brought together and welded to form the hermetical seal around the components.

In one end of the encapsulation is shown a connection body 3 for connecting of leads (not shown), which are inserted and connected to the pacemaker via connecting bores 4. The connection body is often made of transparent plastic to facilitate for the user to see whether the connection is correctly performed or not. The leads are adapted to bring the pacemaker in communication with the heart. Between the connection body 3 and the encapsulation is provided a gas and liquid tight feed through 5 for connecting the leads electrically with the electronic circuits inside the encapsulation.

In FIG. 1 is depicted an RF-circuit board 6, which is equipped with circuitry and components for allowing radio frequency communication between the pacemaker and an external RF-device (not shown). To enable the RF-communication, an antenna 7 is connected to the RF-circuit board 6. Since the shell wall 2 of the encapsulation serves as a radio shielding, the antenna has to be positioned outside of the encapsulation. The connection between the RF-circuit board and the antenna is accomplished by means of a feed through 8 in the encapsulation wall 2.

Referring now to FIG. 2, wherein the feed through 8 and the RF-circuit are shown in a separated state. The feed through comprises an annular sleeve 9 having an inner and outer annular flange 10 and 11, respectively, in its outer end. The sleeve is mounted in a hole in the encapsulation wall 2 such that the encapsulation wall is positioned in the space between the inner and outer flange 10, 11 and welded to establish a gas and liquid tight joint.

In a bore defined by the sleeve 9, a conductor 12 is positioned concentric with the sleeve. To accomplish a hermetical seal between the conductor 12 and the sleeve 9, the conductor is embedded in an electrically insulating molding compound 13, preferably a ceramic, which is filled into the space between the conductor and the sleeve and cured. To further improve the sealing properties, it is also common practice to braze with a metal, preferably gold, in the junction between the molding compound and the sleeve as well as between the molding compound and the connector, respectively.

The conductor 12 and the antenna 7 can be manufactured of one single, integral lead, which functions as an antenna outside the encapsulation and merely as a conductor in the area within the feed through, connecting the antenna with the RF-circuit board. However, the conductor and the antenna could also be assembled of two separate pieces, which are welded or brazed together somewhere outside the encapsulation.

The molding compound 13 is terminated well before the inner end of the sleeve 9 such that an internal cavity 14 is formed around the conductor 12 in the inner end of the sleeve. It is preferred that the sleeve extends at least the same distance as the conductor into the interior of the encapsulation. In this way the sleeve will completely surround the conductor and provide a very effective shielding.

As evident from FIG. 2, the RF-circuit board 6 is, in the embodiment shown, provided with at least two inner, resilient connector pins 15 and two outer, resilient connector pins 16. The connector pins in each pair are resiliently urged towards each other and have their longitudinal extension essentially in parallel to the conductor. The connector pins are moreover curved in the longitudinal direction to facilitate introduction of the conductor and the sleeve, respectively, between each pair of connector pins.

Reference is now made to FIG. 3 in which is depicted the situation when the RF-circuit board is mounted in its place in the encapsulation, i.e. the RF-circuit board is positioned close to or in contact with the feed through sleeve 9. In this position the end portion of the conductor 12 is inserted between the inner connector pins 15, which have been resiliently displaced a short distance from each other, such that the connector pins engages and abuts the surface of the conductor and a reliable electric contact has been established between the inner connector pins and the conductor. In a corresponding way the end portion of the sleeve 9 is inserted between the outer connector pins 16, which have been resiliently displaced a short distance from each other, such that the connector pins engages and abuts the outer surface of the sleeve and a reliable electric contact has been established between the outer connector pins and the sleeve.

In this way is established a reliable connection between the RF-circuit board and the antenna which advantageously can be made with very small dimensions. In an exemplary embodiment, the outside diameter of the sleeve at the inner end, is only about 3 mm and the total length of the sleeve is 2.8 mm. This has to effect that the RF-circuit board may be positioned only about 2 mm from the inner surface of the encapsulation wall. Despite this the connection is made reliable and the shielding sleeve may surround the conductor essentially completely all the way to the surface of the RF-circuit board.

In FIG. 4 is shown an alternative embodiment of the connection according to the invention. Here, the single connector pin 15, for connecting the conductor 12 to the RF-circuit board, is curved or V-shaped and is adapted to engage the end face of the conductor with a substantial axial force. This manner of accomplishing the electric contact between the conductor and the RF-circuit board, may be used as a substitute for connection by means of the previously described connector pins 15 essentially in parallel to the conductor, or as a combination of the two. It is to be understood that the curved connector pin do not necessarily have to be V-shaped. It could be U-shaped, trapezoid or have any other suitable form as well.

Yet another alternative embodiment of the invention is disclosed in FIG. 5. Also here the connector pin is curved in a V-shape. However, the upper part is provided with a hole 17 having a slightly larger diameter than the conductor 12, wherein the hole is somewhat misaligned in relation to the conductor in a state prior to connection. When the conductor meets the connector pin, the latter will be deformed such that the hole 17 and the conductor will subsequently be aligned and the conductor will slide into the hole. When this occurs, the connector pin will spring back a bit such that the hole will grip around the conductor and prevent pulling out of the conductor from the hole.

Although modifications and changes may be suggested by those skilled in the art, it is the intention of the inventors to embody within the patent warranted heron all changes and modifications as reasonably and properly come within the scope of their contribution to the art.

We claim as our invention:

1. Medical implantable device comprising a hermetically sealed, radio shielded encapsulation, which is adapted to be implanted inside living tissue, and an RF-circuit board positioned inside the encapsulation for communication with an RF-device outside the tissue, the RF-circuit board being connectible to an antenna located outside of the encapsulation, via at least one hermetical feed through in form of at least one conductor passed through a wall portion of the encapsulation in a liquid and gas tight manner and electrically insulated from the encapsulation, the RE-circuit board comprising at least one connector pin which is resilient or resiliently mounted on the RF-circuit board, to cause the connector pin, in a mounted state of the RF-circuit board in the encapsulation, to resiliently engage the conductor and electrically connects the conductor with the RF-circuit board, and a shielding sleeve that surrounds the conductor and protrudes essentially the same distance as the conductor or longer, the shielding sleeve being connected to the RF-circuit board by at least one resilient or resiliently mounted connector pin.

2. Medical implantable device according to claim 1, comprising an anvil member which is located on an opposite side of the conductor in relation to the connector pin.

3. Medical implantable device according to claim 2, wherein the anvil member is a resilient or resiliently mounted connector pin.

4. Medical implantable device according to claim 1 wherein each connector pin is directed essentially in parallel to the conductor.

5. Medical implantable device according to claim 4, comprising two or more connector pins.

6. Method for connecting an RF-circuit inside a hermetically sealed, radio shielded encapsulation, to an antenna located outside the encapsulation, comprising the steps of;
providing at least one hermetical feed through connection in the form of at least one conductor passed through a wall portion of the encapsulation in a liquid and gas tight manner and electrically insulated from the encapsulation;
providing at least one connector pin on the RF-circuit board, which is resiliently mounted on the RF-circuit board; and
mounting the RF-circuit in the encapsulation by moving it towards the feed through connection in a direction straining the connector pin towards the conductor such that the connector pin resiliently engages the conductor.

7. Method according to claim 6, comprising straining the connector pin in a radial direction in relation to the conductor.

* * * * *